(12) United States Patent
Evans

(10) Patent No.: US 8,603,055 B1
(45) Date of Patent: Dec. 10, 2013

(54) CATHETER BAG DEVICE

(76) Inventor: Nancy K. Evans, Brunswick, MD (US)

( * ) Notice: Subject to any disclaimer, the term of this patent is extended or adjusted under 35 U.S.C. 154(b) by 1753 days.

(21) Appl. No.: 11/490,720

(22) Filed: Jul. 21, 2006

(51) Int. Cl.
*A61M 1/00* (2006.01)

(52) U.S. Cl.
USPC .......................................... 604/317; 604/329

(58) Field of Classification Search
USPC .................................. 604/317, 329
See application file for complete search history.

(56) References Cited

U.S. PATENT DOCUMENTS

| | | | |
|---|---|---|---|
| 4,145,763 A | 3/1979 | Abrams et al. | |
| 4,173,979 A * | 11/1979 | Odis | 604/327 |
| 4,888,005 A | 12/1989 | Dingeman et al. | |
| 4,997,426 A | 3/1991 | Dingeman et al. | |
| 5,439,456 A * | 8/1995 | Fabricant | 604/327 |
| 5,662,630 A | 9/1997 | Raynie | |
| 6,014,777 A | 1/2000 | Gupton | |
| 6,460,187 B1 | 10/2002 | Siegel | |
| 6,468,254 B2 | 10/2002 | Gupton | |
| 6,647,552 B1 | 11/2003 | Hogan | |
| 6,736,803 B2 | 5/2004 | Cawood | |
| 2003/0032944 A1 | 2/2003 | Cawood | |

* cited by examiner

*Primary Examiner* — Kevin C Sirmons
*Assistant Examiner* — Deanna K Hall
(74) *Attorney, Agent, or Firm* — Sara Centioni Kanos; Nexsen Pruet, LLC

(57) ABSTRACT

A catheter bag having an apron made of opaque material. The apron can be part of the catheter bag at one end and can be detachably secured to the bag at an opposing end using means for attaching.

23 Claims, 4 Drawing Sheets

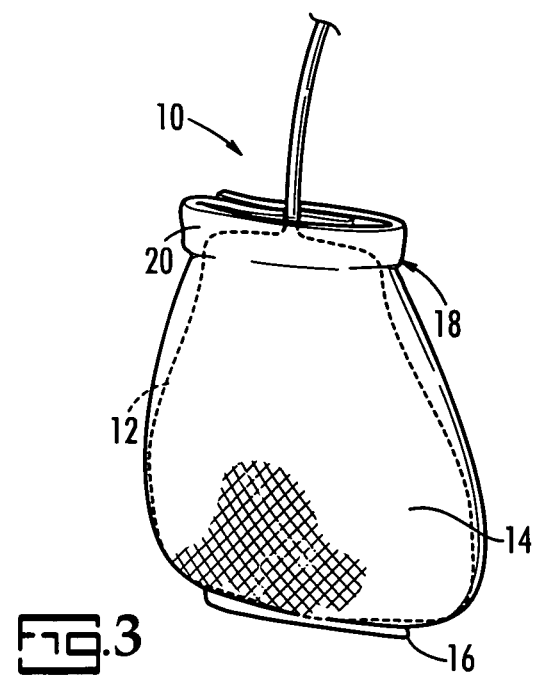
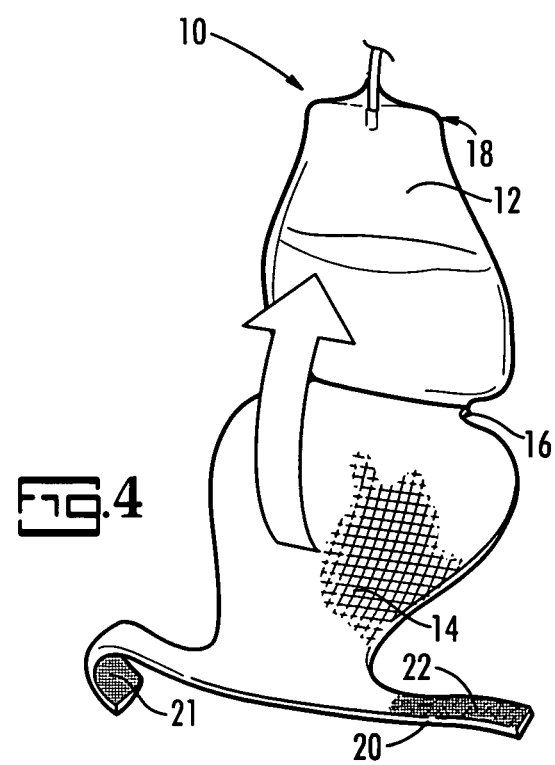

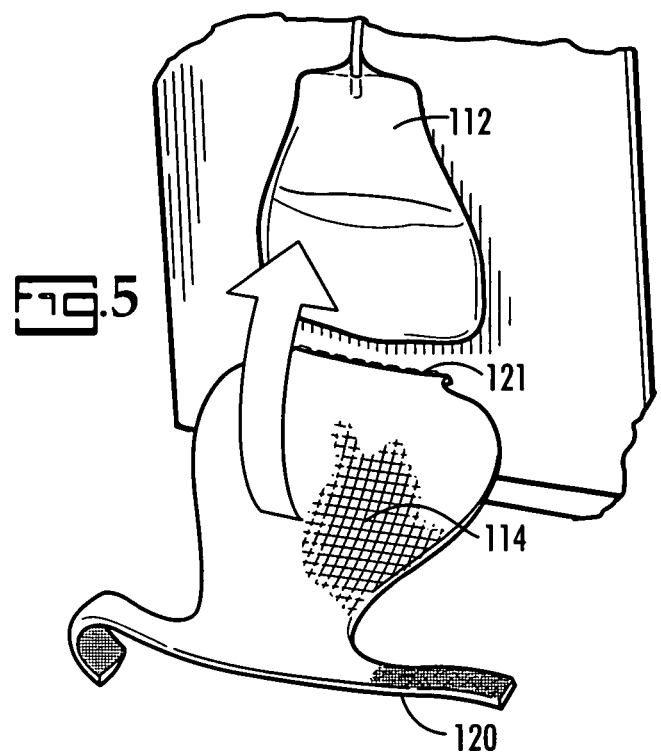
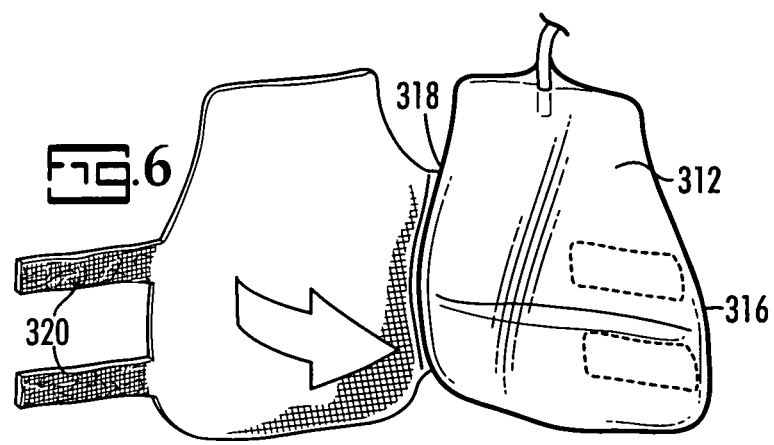
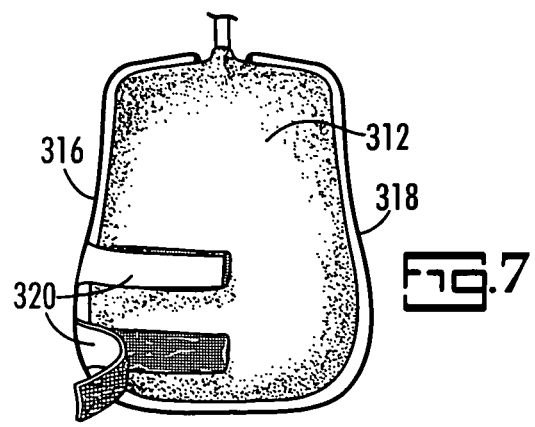

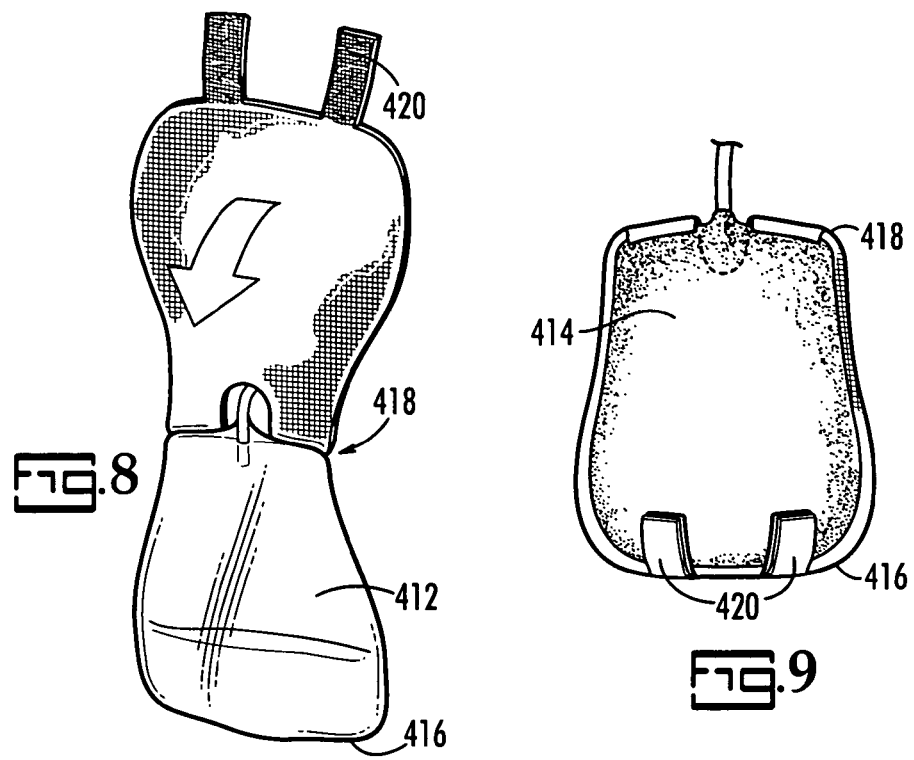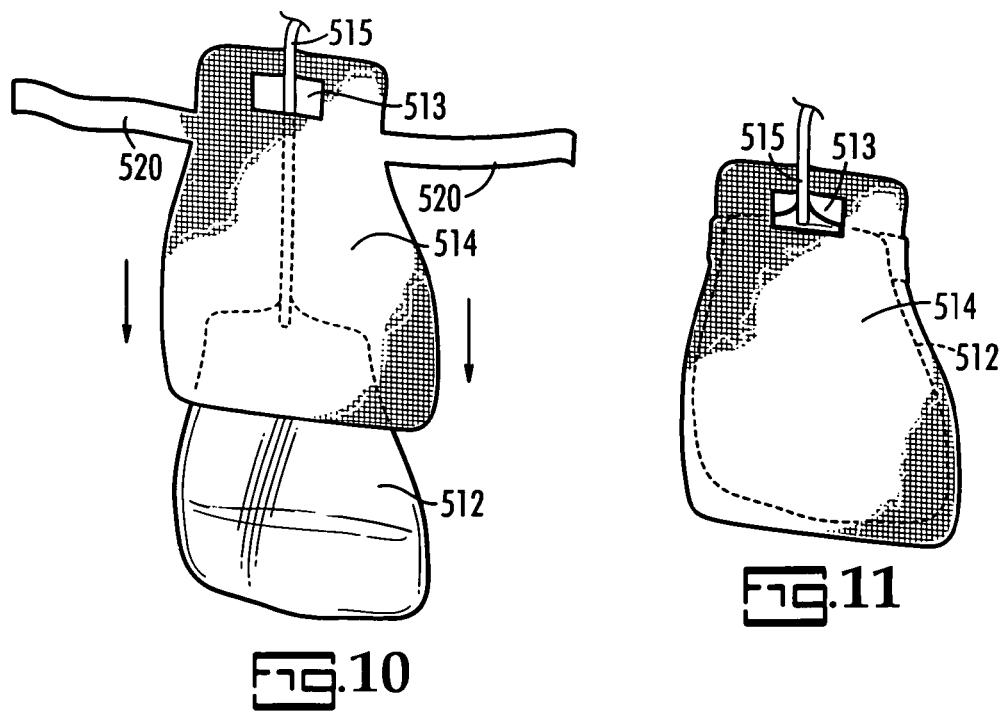

CATHETER BAG DEVICE

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO A SEQUENCE LISTING, A TABLE, OR A COMPUTER PROGRAM LISTING COMPACT DISC APPENDIX

Not Applicable.

BACKGROUND OF THE INVENTION

Urinary catheter devices are widely used in the health care industry. Whereas these devices are both convenient and necessary in many medical settings, they leave much to be desired in terms of privacy and dignity to the patient employing the catheters. Typical urinary catheters includes a flexible catheter drainage tube that is connected to a urinary discharge or drainage bag, which collects the urine as it is passed by the patient. These bags are made of clear or transparent materials on one side so that the contents of the bags can be readily observed. It is this visibility that can cause those using catheter bags discomfort and embarrassment.

Thus far, various devices have been used to address the issue of patient privacy. For example, privacy garments exist that can enhance patient dignity. Additionally, the catheter bags can be placed into purses or outer bags. These devices, however, are not ideal for those caring for the patient. Extracting and replacing catheter bags from these contraptions can be both time consuming and complicated.

Accordingly, there exists a need for catheter bag device that can provide patient privacy without placing undue burden on those caring for the patient.

SUMMARY OF THE INVENTION

The following presents a simplified summary of the invention in order to provide a basic understanding of some aspects of the invention. This summary is not an extensive overview of the invention. It is not intended to identify key or critical elements of the invention or to delineate the scope of the invention. Its sole purpose is to present some concepts of the invention in a simplified form as a prelude to the more detailed description that is presented later.

According to its major aspects and briefly stated, the present invention includes a catheter bag having an apron made of opaque material. The apron can be part of the catheter bag at one end and can be detachably secured to the bag at an opposing end using means for attaching.

A feature of the present invention includes the use of a catheter bag apron made of opaque material. The opaque apron can provide sufficient privacy for a patient by covering the contents of the catheter bag. Furthermore, the apron can be easily moved so that those caring for the patient can view the contents of the catheter bag.

Another feature of the present invention include the use of a catheter bag apron that is part of the catheter bag and that is detachably secured at one end. This feature provides both convenience and ease to those monitoring and maintaining the catheter bags. One can simply unfasten the attaching means and let the apron drop or lower the apron from the catheter bag while observing its contents.

Other features and advantages of the present invention will be apparent to those skilled in the art from a careful reading of the Detailed Disclosure of the Preferred Embodiments presented below and accompanied by the drawings.

BRIEF DESCRIPTION OF THE DRAWINGS

In the drawings,

FIG. 3 illustrates a perspective view of a catheter bag device according to an alternative embodiment of the present invention;

FIG. 4 illustrates a perspective, front view of a catheter bag device according to an alternative embodiment of the present invention;

FIG. 5 illustrates a back view of a catheter bag device according to an alternative embodiment of the present invention;

FIG. 6 illustrates a perspective, front view of a catheter bag device according to an alternative embodiment of the present invention;

FIG. 7 illustrates a back view of a catheter bag device according to an alternative embodiment of the present invention;

FIG. 8 illustrates a front, perspective view of a catheter bag device according to an alternative embodiment of the present invention;

FIG. 9 illustrates a back view of a catheter bag device according to an alternative embodiment of the present invention FIG. 10 illustrates a front, perspective view of a catheter bag device according to an alternative embodiment of the present invention; and FIG. 11 illustrates a front, perspective view of a catheter bag device according to an alternative embodiment of the present invention.

DETAILED DESCRIPTION OF THE PREFERRED EMBODIMENTS

Figure 1:
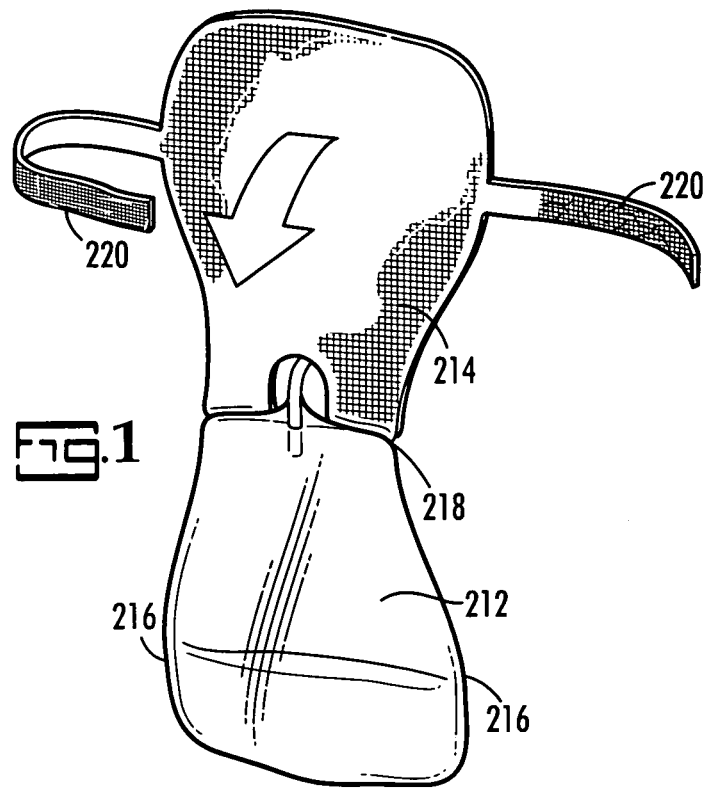
FIG. 1 illustrates a perspective view of a catheter bag device according to a first embodiment of the present invention.
Figure 2:
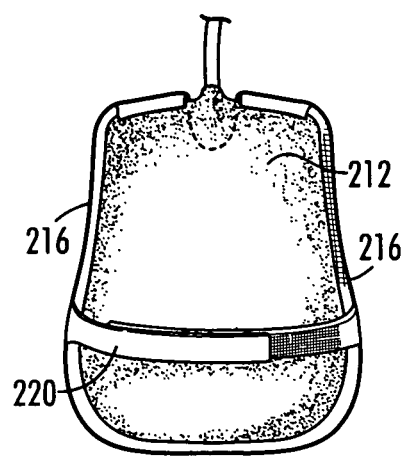
FIG. 2 illustrates a perspective view of a catheter bag device according to a first embodiment of the present invention.

A first embodiment of the present invention is shown in FIGS. 1-2. As shown, a catheter bag 212 includes an apron 214 can be attached at the top end 218 of the catheter bag 212 and detachably secured along side edges 216 of the catheter 212. As shown, the apron 214 can include means for attachment 220 that is dimensioned to wrap around the side edges 216 of the catheter 212. In particular, the attaching means 220 can include strips along opposing side edges that can be overlapped or connected once they are wrapped around the catheter 212. The attaching means 220 of the apron 214 can include any suitable fastener, such as hook and loop fasteners, snaps, ties, or slide fasteners. Additionally, the attaching means can include pliable, but stiff members, such as metal strips, that can form an attachment around the side edges 216 of the catheter 212.

As shown in FIGS. 3-4, a second embodiment of the present invention includes catheter bag device 10 having a catheter bag 12 connected to an apron 14 at one end 16 that is detachably secured to the catheter bag 12 at an opposing end 18 by means for attachment 20. The catheter bag 12 can be any standard type of bag used in the medical and health industry to collect fluids from catheter tubes such as urine. Furthermore, the catheter bag 12 can be used in any setting requiring the collection of fluids and can be easily transported with or by the patient. Typically, the catheter bags 12 will be generally round or pear-shaped and flat. Accordingly, the apron 14 can provide covering or shielding to one side of the catheter bag 12. Further, the catheter bag 12 can be made of clear or transparent material on one side and of opaque material on the other side. The apron 14 can provide covering over the clear side of the catheter bag 12.

The apron 14 of the present invention is preferably made of material that is sufficiently opaque to obstruct the view of whatever it is covering. Any materials exhibiting this property can be used, including natural and synthetic fabrics, plastics, or leathers. Moreover, the materials used can be pliable and lightweight so that the apron can be easily moved and handled without contributing excess weight to the catheter bag 12. As further shown, the apron 14 is dimensioned to completely cover the outer edges of the catheter bag 12 when it is in a secured position.

The attaching means 20 of the apron 14 can include any suitable fastener, such as hook and loop fasteners, snaps, ties, or slide fasteners. Although various dimensions for the attaching means 20 can be employed, the attaching means 20 can be dimensioned to wrap around the top portion or edge of the catheter bag 12 to provide both a secure attachment and to better conceal the contents of the bag 12. For example, attaching means 20 can include first strip 21 and second strip 23 that can be overlapped or connected once wrapped around the top portion of the catheter bag 12 to provide attachment.

As discussed, a feature of the present invention includes the use of a catheter bag apron 14 made of opaque material. The opaque apron 14 can provide sufficient privacy for a patient by covering the contents of the catheter bag 12. Furthermore, the apron 14 can be easily moved so that those caring for the patient can view the contents of the catheter bag. Additionally, because the apron 14 is detachably secured at one end of the bag 12, those maintaining the bag 12 can conveniently and easily monitor the bag's contents. As illustrated, one can simply unfasten the attaching means 20 and allow the apron 14 to drop or lower the apron 14 from the catheter bag 12 while observing its contents.

In a third alternative embodiment shown in FIG. 5, the apron 114 is completely detachable from the catheter bag 112. Depending on the demand of privacy and quantities of catheter bags 112, it may be useful to provide a detachable apron 114 as previously discussed that can be used in combination with more than one catheter bag 112. Accordingly, the apron 114 can be detachably secured at one end of the catheter bag 112 by means for attachment 120. One can therefore simply lift the apron 114 to view the bag's contents. Alternatively, to provide a more secure cover to the catheter bag 112, the apron 114 can also be detachably secured an opposing end of the catheter bag 112 by a second means for attachment 121, such as a reusable adhesive strip or tape. As further shown, the catheter bag 112 can be used by itself, or it can be used in conjunction with other devices employed during the treatment of the patient.

In a fourth alternative embodiment shown FIGS. 6-7, the apron 314 can be attached at a first side edge 318 of the catheter bag 312 and detachably secured along a second, opposing side edge 316 of the catheter 312. As shown, the apron 314 can include means for attachment 320 that is dimensioned to wrap around the second side edge 316 of the catheter 312. The attaching means 320 of the apron 314 can include any suitable fastener, such as hook and loop fasteners, snaps, ties, or slide fasteners. Additionally, the attaching means can include pliable, but stiff members, such as metal strips, that can form an attachment around the second side edge 316 of the catheter 312.

In a fifth alternative embodiment shown in FIGS. 8-9, the apron 414 can be attached at the top end or edge 418 of the catheter bag 412 and detachably secured at the bottom end or edge 416 of the catheter 412. As shown, the apron 414 can include means for attachment 420 that is dimensioned to wrap around the bottom edge 416 of the catheter 412. The attaching means 420 of the apron 414 can include any suitable fastener, such as hook and loop fasteners, snaps, ties, or slide fasteners. Additionally, the attaching means can include pliable, but stiff members, such as metal strips, that can form an attachment around the side edges 416 of the catheter 412.

In a sixth alternative embodiment shown in FIGS. 10-11, the apron 514 can include an aperture 513 that is dimensioned to receive a catheter drainage tube 515. Once engaged with the drainage tube 515, the apron 514 is secured to the catheter bag 516, and can be raised and lowered when needed. Furthermore, at the top edge of the apron 514 can be included means for attachment 520 that can be dimensioned to wrap around the top portion or edge of the catheter bag 512 to provide both a secure attachment and to better conceal the contents of the bag 512.

Those skilled in the art of catheter bag devices will recognize that many substitutions and modifications can be made in the foregoing preferred embodiment with departing from the spirit and scope of the present invention.

What is claimed is:

1. A device, comprising:
a catheter bag having a first end and a second end; and
an apron made of an opaque material that is connected only to said catheter bag at said first end and that is detachably secured only to said catheter bag at said second end, wherein said apron covers only one side of said catheter bag, and wherein said apron covers contents of said catheter bag from view.

2. The device as recited in claim 1, wherein said apron is dimensioned to cover the outer edges of said catheter bag when said apron is secured to said catheter bag.

3. The device as recited in claim 1, wherein said first end is the bottom end of said catheter bag.

4. The device as recited in claim 3, wherein said apron is detachably secured to said catheter bag at said second end by means for attaching.

5. The device as recited in claim 4, wherein said attaching means is a hook and loop fastener.

6. The device as recited in claim 4, wherein said attaching means is a snap fastener.

7. The device as recited in claim 4, wherein said attaching means is a tie fastener.

8. The device as recited in claim 4, wherein said attaching means is a slide fastener.

9. The device as recited in claim 4, wherein said attaching means is dimensioned to wrap around the top edge of said catheter bag.

10. The device as recited in claim 1, wherein said first end is the top end of said catheter bag.

11. The device as recited in claim 10, wherein said attaching means is dimensioned to wrap around the bottom edge of said catheter bag.

12. The device as recited in claim 10, wherein said attaching means is dimensioned to wrap around the opposing side edges of said catheter bag, and wherein said attaching means is between said first end and said second end of said catheter bag.

13. The device as recited in claim 1, wherein said opaque material is fabric.

14. The device as recited in claim 1, wherein said opaque material is plastic.

15. The device as recited in claim 1, wherein said opaque material is leather.

16. A device, comprising:
    a catheter bag having a first end and a second end; and
    an apron made of an opaque material that is detachably secured only to said catheter bag at said first end by a first means for attaching, said apron being dimensioned to cover the outer edges of said catheter bag, wherein said apron covers only one side of said catheter bag, and wherein said apron covers contents of said catheter bag from view.

17. The device as recited in claim 16, wherein said apron is detachably secured to said catheter bag at said second end by a second means for attaching.

18. The device as recited in claim 17, wherein said second means for attaching is an adhesive strip.

19. The device as recited in claim 17, wherein said second means for attaching is tape.

20. A device, comprising:
    a catheter bag having a first side edge and an opposing second edge; and
    an apron made of an opaque material that is connected only to said catheter bag at said first side edge and that is detachably secured only to said catheter bag at said second side edge, wherein said apron covers only one side of said catheter bag, and wherein said apron covers contents of said catheter bag from view.

21. A device, comprising:
    a catheter bag connected to a drainage tube; and
    an apron having an aperture dimensioned to receive said drainage tube, wherein said apron includes a means for attachment that can secure said apron only to said catheter bag, wherein said apron covers only one side of said catheter bag, and wherein said apron covers contents of said catheter bag from view.

22. A device, comprising:
    a catheter bag having a first end and a second end; and
    an apron made of an opaque material that is connected only to said catheter bag at said first end and that is detachably secured only to said catheter bag at said second end, wherein said apron covers only one side of said catheter bag so that the contents of said catheter bag are covered from view, and wherein said contents are viewable without detaching said apron.

23. A device, comprising:
    a catheter bag having a first end and a second end; and
    an apron made of an opaque material that is connected only to said catheter bag at said first end and that is detachably secured only to said catheter bag at said second end, wherein said apron covers only one side of said catheter bag so that the contents of said catheter bag are covered from view, wherein said one side of said catheter, and wherein said one side opposes the side on which said catheter bag is attached for use.

\* \* \* \* \*